(12) United States Patent
Liporace et al.

(10) Patent No.: US 10,143,557 B1
(45) Date of Patent: Dec. 4, 2018

(54) TOTAL ELBOW ARTHROPLASTY APPARATUS AND METHOD

(71) Applicants: Frank A. Liporace, Englewood Cliffs, NJ (US); Richard S. Yoon, New York, NY (US)

(72) Inventors: Frank A. Liporace, Englewood Cliffs, NJ (US); Richard S. Yoon, New York, NY (US)

( * ) Notice: Subject to any disclaimer, the term of this patent is extended or adjusted under 35 U.S.C. 154(b) by 0 days.

(21) Appl. No.: 15/197,684

(22) Filed: Jun. 29, 2016

Related U.S. Application Data

(60) Provisional application No. 62/185,825, filed on Jun. 29, 2015.

(51) Int. Cl.
*A61F 2/38* (2006.01)
*A61F 2/30* (2006.01)

(52) U.S. Cl.
CPC .. *A61F 2/3804* (2013.01); *A61F 2002/30626* (2013.01); *A61F 2002/30672* (2013.01); *A61F 2002/30677* (2013.01); *A61F 2002/3813* (2013.01)

(58) Field of Classification Search
CPC .. A61F 2/38; A61F 2/3804; A61F 2002/3809; A61F 2002/3813; A61F 2002/3818; A61F 2002/3822; A61F 2002/3831
See application file for complete search history.

(56) References Cited

U.S. PATENT DOCUMENTS

| | | | | |
|---|---|---|---|---|
| 2,696,817 A | * | 12/1954 | Prevo | A61F 2/3804 606/301 |
| 5,443,516 A | * | 8/1995 | Albrektsson | A61F 2/384 606/70 |
| 2010/0211120 A1 | * | 8/2010 | Bonutti | A61B 17/0401 606/86 R |

* cited by examiner

*Primary Examiner* — Brian Dukert (57) ABSTRACT

A medical implant apparatus for total elbow arthroplasty is provided. The apparatus includes: a first rod member comprising a first nut, an eye hook, a first end, and a second end, wherein the first nut is disposed at the first end and the eye hook is disposed at the second end; a second rod member rotatably coupled to the first rod member, the second rod member comprising a first linear portion, a second linear portion, and an arcuate portion disposed between the first linear portion and the second linear portion, the arcuate portion being configured to form a predetermined angle between the first rod member and the second rod member; a positioning nut coupled to the first linear portion of the second rod member; and an aperture disposed in the eye hook.

20 Claims, 6 Drawing Sheets

TOTAL ELBOW ARTHROPLASTY APPARATUS AND METHOD

CROSS-REFERENCE TO RELATED APPLICATION

This application claims priority to U.S. Provisional Patent Application No. 62/185,825 filed on Jun. 29, 2015, the entire content of which is incorporated herein by reference.

BACKGROUND

The number of total elbow arthroplasty (TEA) procedures being performed in the United States continues to increase, especially with improving outcomes and expanding indications. Unlike lower extremity arthroplasty, there is a noticeable lack of literature regarding the management of periprosthetic infection and/or fracture about TEA. Recommended strategies to treat periprosthetic infection have included irrigation and debridement (I&D), resection arthroplasty, single and two-stage revision, arthrodesis, and/or amputation. However, most recommended strategies are not supported by high levels of evidence and thus, a lack of a consensus treatment algorithm remains.

Acute infections can be treated successfully with aggressive, early I&D with long-term intravenous (IV) antibiotics. Yamaguchi et al. recommended identification of the causative organism, as retention of implants seeded with *S. epidermidis* had a high risk of failure with I&D and IV antibiotics alone. A more recent study by Spormann et al., however, reported contrasting results noting 100% acute eradication, however, all of their patients were identified and treated less than three weeks from their index procedure. For chronic infections, there leaves only a few options: single-stage or two-stage explant/replant, resection arthroplasty, or arthrodesis.

Arthrodesis, considered a salvage procedure in almost any setting, is the least desired and the least successful in the setting of TEA infection. Arthrodesis in general severely debilitates the upper extremity being in a fixed position, but in the setting of TEA infection can yield poor results. Otto et al. in a recent case series reported inability to achieve any bony union for failed TEA secondary to deep infection, leaving all their patients with a resection arthroplasty. The authors concluded that even arthrodesis should not be considered an option in the setting of TEA infection.

Unlike the data available for periprosthetic fracture and infection in THA and TKA, the literature to devise an accepted algorithm for periprosthetic fracture and infection for TEA is unavailable. Instead, most recommendations come from level IV studies from the higher volume TEA surgeons, reporting their preferred methods and outcomes in treating periprosthetic infection.

SUMMARY

A medical implant apparatus for total elbow arthroplasty is provided. The apparatus includes: a first rod member comprising a first nut, an eye hook, a first end, and a second end, wherein the first nut is disposed at the first end and the eye hook is disposed at the second end; a second rod member rotatably coupled to the first rod member, the second rod member comprising a first linear portion, a second linear portion, and an arcuate portion disposed between the first linear portion and the second linear portion, the arcuate portion being configured to form a predetermined angle between the first rod member and the second rod member; a positioning nut coupled to the first linear portion of the second rod member; and an aperture disposed in the eye hook.

According to further embodiments: at least a portion of the first linear portion is disposed within the aperture; the eye hook is disposed between the positioning nut and at least a portion of the arcuate portion; the first rod member is configured to be coupled to the second rod member such that the aperture of the eye hook is slidable along the first linear portion; the predetermined angle between the first rod member and the second rod member is substantially 90 degrees; the positioning nut is configured to adjust a position of the aperture of the eye hook along the first linear portion; the first linear portion is secured to the first rod member by only the positioning nut and the eye hook; a securing nut is coupled to the first linear portion such that the aperture of the eye hook is between the positioning nut and the securing nut.

A kit for performing total elbow arthroplasty is provided. The kit includes: the medical implant apparatus as described above; and an antibiotic-loaded substrate coated on the medical implant apparatus.

A method of treating a patient in need of total elbow arthroplasty is provided. The method includes: providing a medical implant apparatus comprising a first rod member that is substantially straight and a second rod member that is substantially straight; bending the second rod member to comprise a first linear portion, a second linear portion, and an arcuate portion; coupling an eye hook, which includes an aperture member, to the first rod member; inserting the first linear portion through the aperture member; coupling a positioning nut to the first linear portion; coating the first rod member and the second rod member with antibiotic-loaded substrate; and implanting total elbow arthroplasty apparatus into the patient's elbow.

According to further embodiments: the second linear portion of the second rod member is bent to correspond the alignment of the patient's proximal ulna and the proximal humerus; the arcuate portion is disposed between the first linear portion and the second linear portion; implantation of the total elbow arthroplasty apparatus includes implanting at least a portion of the first rod member into the patient's humerus and at least a portion of the second linear portion of the second rod into the patient's ulna; an infected elbow prosthesis is removed prior to implantation of the medical implant apparatus; after the medical implant apparatus is implanted for a predetermined period of time, the medical implant apparatus is removed and a permanent total elbow arthroplasty prosthesis is implanted; the first rod member is rotatably coupled to the second rod member; and the medical implant apparatus provides the patient with an elbow range of motion of 0-145 degrees.

BRIEF DESCRIPTION OF THE DRAWINGS

The above and other aspects, features and advantages of certain embodiments will be more apparent from the following detailed description taken in conjunction with the accompanying drawings, in which.

DETAILED DESCRIPTION

The following detailed description of certain embodiments will be made in reference to the accompanying drawings. In the detailed description, explanation about related functions or constructions known in the art are omitted for the sake of clearness in understanding the concept of the invention, to avoid obscuring the invention with unnecessary detail.

Reference to individual embodiments, whether by number of embodiment or relevant feature of the embodiment, is used for convenience in describing such embodiments. Moreover, reference to individual embodiments does not indicate that any of such embodiments are preferred over any other embodiments. Furthermore, each individual embodiment may be combined with any other individual embodiment whether or not expressly stated.

Embodiments of the invention described herein provide a medical implant apparatus for total elbow arthroplasty, methods of treating a patient in need of total elbow arthroplasty, and a kit for total elbow arthroplasty. When a patient is diagnosed with an infected total elbow replacement or an infected elbow with bone loss, the medical implant apparatus according to the embodiments described herein provide treatment thereof. In certain embodiments, the medical implant apparatus provides a temporary elbow implant, which allows the patient's elbow to heal from infection and/or bone loss until a permanent elbow prosthesis is implanted. The medical implant apparatus provides the patient with a temporary spacing device that enables healing while also allowing for motion of the patient's arm leading to improved function and improved eradication rate of infection. Current temporary elbow implant prosthetics, also referred to as "spacers," do not allow for motion of the patient's arm, whereas the medical implant apparatus described herein provides the patient with a functional arm while waiting for their bone to heal in order to implant a permanent prosthetic. Accordingly, embodiments of the invention described herein provide a viable treatment option for many infections, including those with bone loss and/or periprosthetic fracture.

Figure 2A:
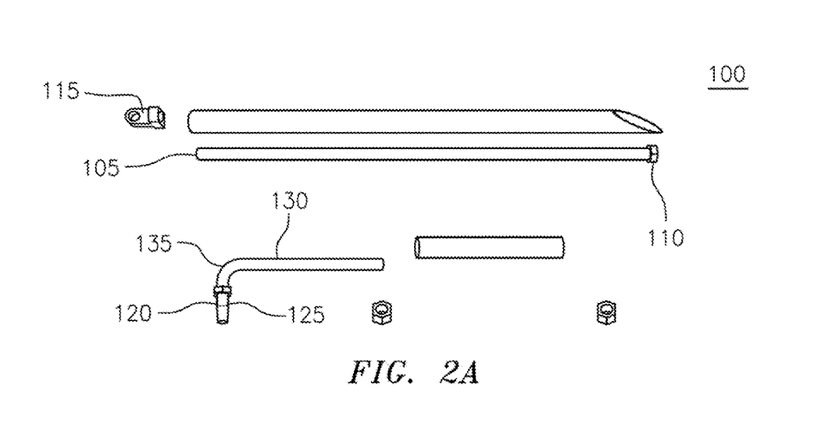
FIGS. 2A-2C: Preparation of the hinged, antibiotic-loaded cement spacer utilized chest tubes, two modified Ilizarov rods and nuts and hooks (A). Construct assembly was performed with the plan for the humeral rod to bypass the site of non-union and span the entire humerus (B). Final coating via chest tubes were performed utilizing an antibiotic ratio of 3 g vancomycin/3.6 g tobramycin per bag of cement (C).
Figure 2B:
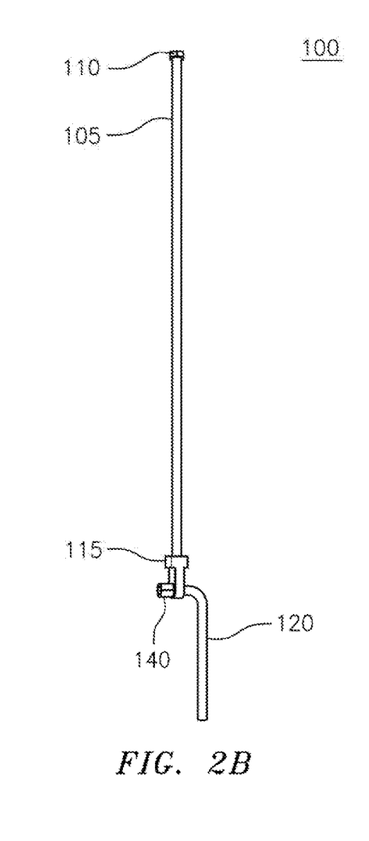
Figure 2C:
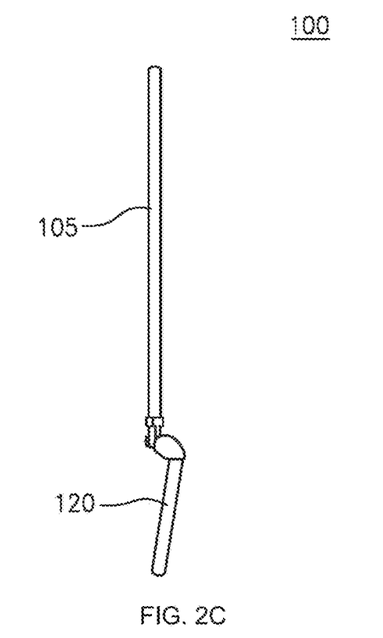
Figure 3B:
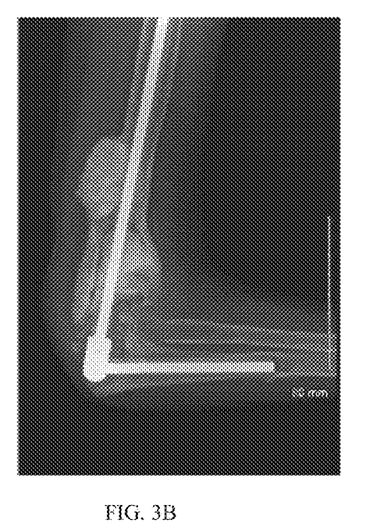
FIGS. 3A-3B: Postoperative anteroposterior (AP) and lateral radiographs following construct placement with the bony void filled with antibiotic-loaded cement.
Figure 3C:
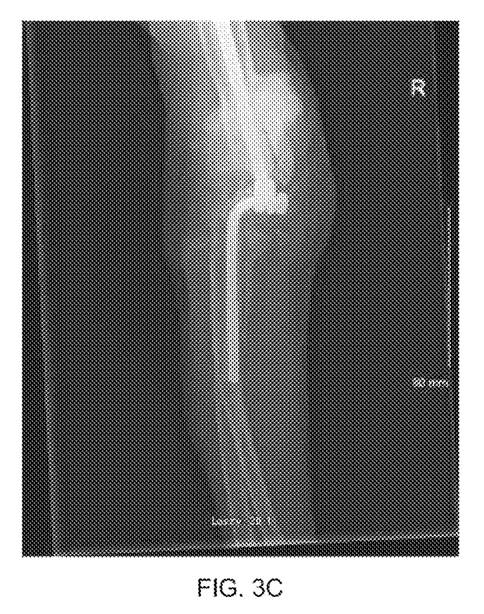

FIGS. 2A-2C illustrate a medical implant apparatus for total elbow arthroplasty 100. The medical implant apparatus includes a first rod member 105. The first rod member may be configured as a cylinder, or other suitable shape. The first rod member is substantially straight, though it may be contoured to correspond to the contour of a patient's humerus. The first rod member includes a first nut 110 disposed at a first end. The first rod member includes an eye hook 115 disposed at a second end extending from the first rod member. The eye hook may extend linearly though, in certain embodiments, the eye hook may extend at an angle of 0-30 degrees in order to correspond to the angle between the patient's humerus and ulna. The eye hook includes an aperture member.

The apparatus further includes a second rod member 120. The second rod member may be configured as a cylinder, or other suitable shape. The second rod member includes a first linear portion 125 and a second linear portion 130. The second rod member includes arcuate portion 135 disposed between the first linear portion 125 and the second linear portion 130. The arcuate portion of the second rod member is configured such that the angle created between the first linear portion and the second linear portion may be adjusted to correspond to the alignment of the proximal ulna and the proximal humerus. In certain embodiments, the arcuate portion of the second rod member may be configured as a substantially 90 degree angle. In further embodiments, the arcuate portion may be configured as a substantially 70-120 degree angle.

The first linear portion of the second rod member includes a positioning nut 140. The first rod member is rotatably coupled to the second rod member. The first linear portion of the second rod member is disposed within the aperture member of the eye hook. The positioning nut prevents the aperture member from sliding off the first linear portion, which would resulting in the first and second rod members no longer being coupled. By tightening and loosening the positioning nut along a threaded end of the first linear portion, the positioning nut also allows a surgeon to adjust the location of where the eye hook's aperture member is positioned on the first linear portion.

In certain embodiments, the first linear portion is secured to the first rod member by only the positioning nut and the eye hook. Thus, the eye hook is configured to rotate around the first linear portion and the eye hook is configured to slide on the first linear portion and the arcuate portion. This configuration of the apparatus allows free movement of the proximal ulna and the proximal humerus.

In certain embodiments, a securing nut is coupled to the first linear portion of the second rod member. The securing nut and the positioning nut secure the aperture member to the first linear portion of the second rod member. The securing nut and the positioning nut secure the aperture member to the first linear portion such that the eye hook does not slide to the arcuate portion, but remains rotatably coupled to the first linear portion. That is, the securing nut and the positioning nut maintain the eye hook on the first linear portion. In this embodiment, the eye hook is configured to rotate around the first linear portion, but the eye hook is not configured to slide on the first linear portion and the arcuate portion.

According to a further embodiment, a kit is provided for performing total elbow arthroplasty. The kit includes the medical implant apparatus described herein. The kit further includes an antibiotic-loaded substrate coated on the medical implant apparatus. The substrate includes bone cement or a suitable molding material. The cement is coated around the first rod member and the second rod member. In certain embodiments, the cement is coated around the second linear portion and the arcuate portion of the second rod member. In certain embodiments, the cement is not coated around the aperture member and the securing nut.

According to a further embodiment, a method of treating a patient in need of total elbow arthroplasty is provided. The method includes providing a first rod member that is substantially straight and a second rod member that is substantially straight. In certain embodiments, the first rod member and the second rod member may be modified Ilizarov rods. The method includes bending the second rod member to have a first linear portion, a second linear portion, and an arcuate portion. The second rod member is bent to correspond the alignment of the patient's proximal ulna and the proximal humerus. The arcuate portion is disposed between the first linear portion and the second linear portion.

The method includes coupling an eye hook, which includes an aperture member, to the first rod member. The method includes inserting the first linear portion through the aperture member and coupling a positioning nut to the first linear portion such that the first rod member is rotatably coupled to the second securing rod. The method further includes coating the first rod member and the second rod member with antibiotic-loaded substrate. The substrate includes bone cement or other suitable molding material.

Antibiotics used in combination with bone cement include vancomycin and tobramycin and other suitable antibiotics. For example, a rifamycin may be administered in conjunction with one or more additional antibiotic agents (e.g., sulfonamides, tetracyclines, aminoglycosides, macrolides, lincosamides, ketolides, fluoroquinolones, glycopeptide antibiotics, and polymyxin antibiotics) such as azithromycin, clarithromycin, erythromycin, gatifloxacin, amoxicillin, metronidazole, penicillin G, penicillin V, methicillin, oxacillin, dicloxacillin, nafcillin, ampicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, carbapenem, cefoxitin, cefmatozole, cefotaxime, ceftriaxone, cefoperazone, ceftazidime, cefixime, cefpodoxime, ceftibuten, cefdinir, cefpirome, cefepime, imipenem, ertapenem, meropenem, astreonam, clavulanate, sulbactam, tazobactam, streptomycin, neomycin, kanamycin, puromycin, gentamicin, amikacin, netilmicin, spectinomycin, sisomicin, dibekalin, isepamicin, tetracycline, chlortetracycline, demeclocycline, minocycline, oxytetracycline, methacycline, doxycycline, telithromycin, lincomycin, clindamycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, moxifloxacin, gemifloxacin, sitafloxacin, daptomycin, garenoxacin, ramoplanin, fusidic acid, faropenem, polymyxin, tigecycline, or trimethoprim). Other suitable antibiotics for use in the method includes quinolones (e.g., moxifloxacin, levofloxacin, gatifloxacin, ciprofloxacin, fleroxacin, and ofloxacin), cotrimoxazole (trimethoprim and sulfamethoxazole), minocycline, fusidic acid, linezolid, nafcillin, teicoplanin ceftriaxone, ceftazidime, cefepime, clindamycin, amoxicillin, ampicillin, carbapenem, and daptomycin.

The coated total elbow arthroplasty apparatus is then implanted into the patient's elbow. Implantation of the total elbow arthroplasty apparatus includes implantation of at least a portion of the first rod member into the patient's humerus and at least a portion of the second linear portion of the second rod into the patient's ulna.

In certain embodiments, the method includes removing an infected elbow prosthesis prior to implantation of the total elbow arthroplasty apparatus. Once the apparatus is implanted for a predetermined period of time, the apparatus is removed and a permanent total elbow arthroplasty prosthesis is implanted. After implantation, the medical implant apparatus provides the patient with an elbow range of motion of 0-145 degrees.

According to a further embodiment, a method of treating a patient in need of total elbow arthroplasty with a two-stage revision is provided. The method includes a first step in which an infected elbow prosthesis is removed from the patient's elbow. The method includes a second step in which a temporary medical implant apparatus is implanted into the patient's elbow for a predetermined period of time. The method includes a third step in which the temporary medical implant apparatus is removed from the patient's elbow and a permanent elbow prosthesis is implanted into the patient's elbow.

Embodiments of the invention described herein were utilized in the following example.

Example

The patient is a 77-year-old female, with hypertension and schizophrenia, who sustained an ipsilateral, comminuted distal humerus and distal radius fracture of her dominant arm after a fall. Initial treatment at an outside institution included open reduction internal fixation of her wrist with concurrent TEA. Her initial postoperative course was largely uncomplicated, except for a bout of cellulitis that occurred 14 weeks postoperatively, and was treated successfully with oral antibiotics. Seven months following her index procedure, however, she sustained another fall, suffering a periprosthetic fracture about the humeral component. Her primary surgeon elected to treat her conservatively in a fracture brace, however, with 4 months of persistent pain and non-progression of fracture healing, the patient required further treatment.

At initial evaluation, the patient was afebrile and denied previous fevers, chills or drainage. Examination noted obvious deformity about her right elbow with tender, non-erythematous, but swollen and intact soft tissue. She was painful throughout her range of motion both passively and actively. Initial laboratory work-up indicated a normal white blood cell (WBC) count, erythrocyte sedimentation rate (ESR), and C-reactive protein (CRP).

Figure 1A:
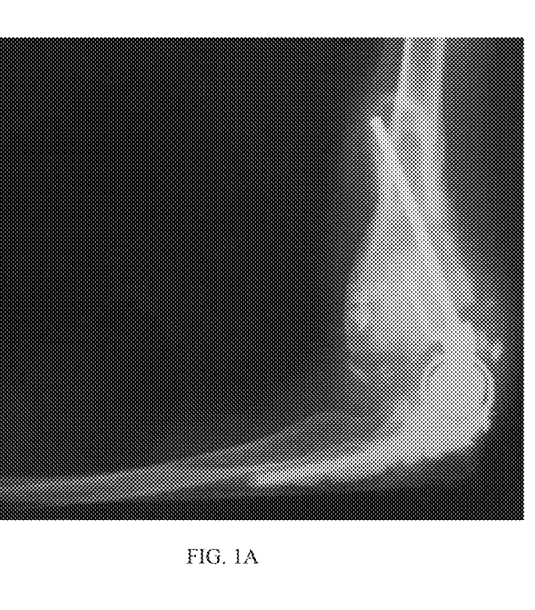
FIGS. 1A-1B: Malunited periprosthetic fracture with a protruding humeral component with noted cortical bone loss, periosteal reaction and medullary canal expansion noted on both radiograph (A) and CT (B).
Figure 1B:
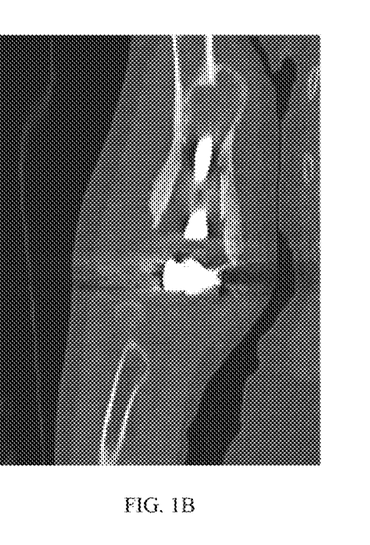

Plain radiographic and computed tomographic (CT) imaging revealed a more severe clinical picture and exhibited a malunited periprosthetic fracture with a protruding humeral component with noted cortical bone loss, periosteal reaction and medullary canal expansion suspicious of concurrent chronic infection. See FIGS. 1A-1B. Chronic pen-implant infection with superimposed osteomyelitis was confirmed with positive triple phase technetium bone scan and radiolabeled WBC nuclear studies.

The patient was brought to the operating room for a planned, two-stage revision. The first stage includes explant of the infected prosthesis via the previously utilized posterior approach, thorough I&D, and placement of our hinged, antibiotic spacer.

Preparation of our hinged, antibiotic spacer utilized two cylindrical rods, such as modified Ilizarov rods, connected using hooks and nuts and contoured to correspond to the alignment of the proximal ulna and the proximal humeral nonunion. The first rod member and the second linear portion of the second rod member may be contoured at an angle of 0-30 degrees. Furthermore, the angle of the aperture member may be adjusted with respect to the first rod member to provide an angle of 0-30 degrees between the first rod member and the second rod member. See FIGS.

2A-2B. The rods were coated with antibiotic-loaded cement (approximately 3 g vancomycin, 3.6 g tobramycin per bag of cement) using chest tubes. See FIG. 2C. Length of the humeral component extended proximally past the surgical neck to span the non-union and bony void. The bony void was filled with additional antibiotic-loaded cement in a Masquelet-type fashion for future bone grafting. The spacer was found to be stable throughout a range of motion of approximately 15-115 degrees, which the patient maintained until the second stage.

Intraoperative cultures were positive for vancomycin resistant *enterococcus*. For 6 weeks, the patient received cefepime 1 g IV q6 hrs and daptomycin 300 mg IV qdaily. Until the second stage replantation, the patient remained in a removable posterior splint and was allowed to perform gentle range of motion (ROM) with a therapist's guidance. Patient's WBC, ESR and CRP all remained normal after a 3-week antibiotic holiday and the patient returned to the OR for definitive reconstruction.

A biologic membrane formed around the antibiotic coated rod. This tissue was carefully dissected and preserved prior to removal of the nail. This membrane was found to have increased vascularity as well as increased markers of osteoblastic lineage. This example confirms that the biologic membrane formed in response to antibiotic cement can be utilized in patients to enhance bone formation in cases of segmental bone loss.

Figure 4:
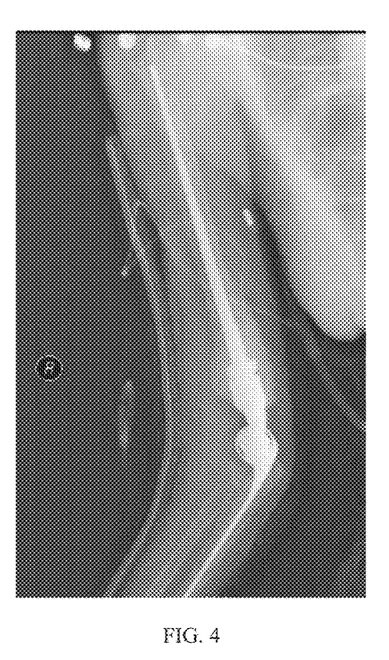
FIG. 4: Immediate postoperative radiograph exhibiting final components in good position with bony healing occurring at the level of distal humerus where the biologic membrane had formed.

Upon re-entry, the biologic membrane was found and preserved. The hinge of the antibiotic-coated apparatus was disengaged and the apparatus was removed without difficulty. Frozen section was negative and a permanent total elbow arthroplasty prosthesis was implanted. Autologous bone graft was placed within the biologic membrane and the membrane was closed around the permanent prosthesis. See FIG. 4.

Figure 5A:
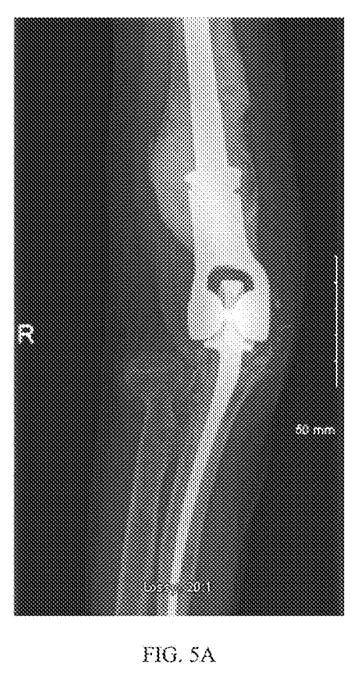
FIGS. 5A-5B: (A) At 6-week and (B) 3 month follow-up, radiographs revealed well-positioned components and continued bony restoration at the level of the biologic membrane.
Figure 5B:
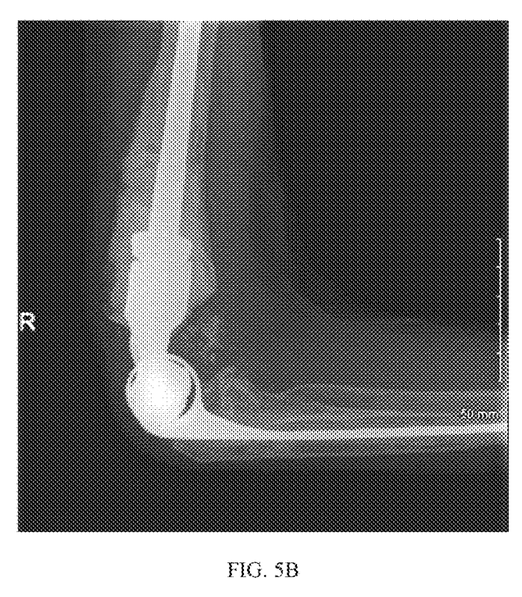
Figure 5C:
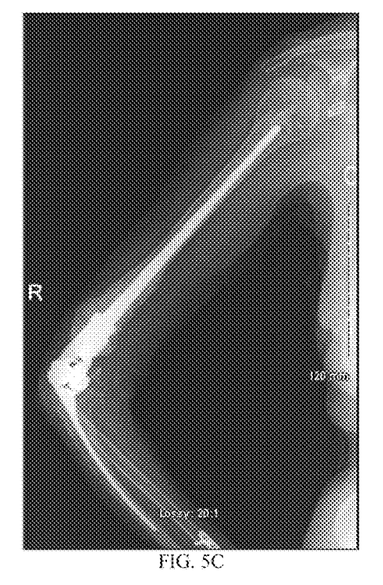
FIGS. 5C-5D: Final radiographs indicate well-positioned components without signs of loosening as well as prominent bone formation about the distal humerus.
Figure 5D:
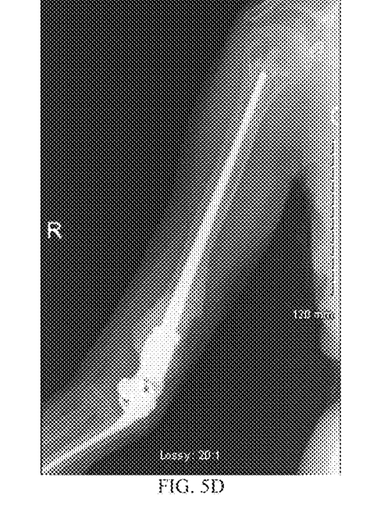

The patient's soft tissues healed without event and the patient returned at her initial postoperative visit with a passive ROM of −5 to 90 degrees. At 6-week and 3 month follow-up, radiographs revealed well-positioned components and continued bony restoration at the level of the biologic membrane. See FIGS. 5A-5B. Active ROM began at 6 weeks and strengthening at 3 months, with the patient continuing to remain pain-free with an active ROM of 10-110 with weight restricted to 5 lbs. Final radiographs indicate well-positioned components without signs of loosening as well as prominent bone formation about the distal humerus. See FIGS. 5C-5D.

The apparatus and method described herein provides several advantages. The apparatus provides mechanical stability that was required after the infected elbow prosthesis was removed. Due to significant bone loss of the distal humerus, as well as non-union of the humeral diaphysis, the apparatus provided stability for elbow range of motion post-operatively and allowed for bone healing. Furthermore, the apparatus eluted a high concentration of local antibiotics to help eradicate infection. Finally, the articulation between the two rods allowed the patient significant ROM and increased function while awaiting permanent prosthesis implantation.

While embodiments of the invention have been shown and described with reference to certain embodiments thereof, it will be understood by those skilled in the art that various changes in form and details may be made therein without departing from the spirit and scope of the invention as defined by the appended claims and equivalents thereof.

What is claimed is:

1. A medical implant apparatus for total elbow arthroplasty, the apparatus comprising:
    a first rod member comprising a first nut, an eye hook, a first end, and a second end, wherein the first nut is disposed at the first end and the eye hook is disposed at the second end;
    a second rod member rotatably coupled to the first rod member, the second rod member comprising a first linear portion, a second linear portion, and d an arcuate portion disposed between the first linear portion and the second linear portion, the arcuate portion being configured to form a predetermined angle between the first rod member and the second rod member;
    a positioning nut coupled to the first linear portion of the second rod member; and
    an aperture disposed in the eye hook,
    wherein the first rod member is configured to be coupled to the second rod member such that, the aperture of the eye hook is slidable along the first linear portion.

2. The medical implant apparatus according to claim 1, wherein at least a portion of the first linear portion is disposed within the aperture.

3. The medical implant apparatus according to claim 2, wherein the eye hook is disposed between the positioning nut and at least a portion of the arcuate portion.

4. The medical implant apparatus according to claim 1, wherein the predetermined angle between the first rod member and the second rod member is substantially 90 degrees.

5. The medical implant apparatus according to claim 1, wherein the positioning nut is configured to adjust a position of the aperture of the eye hook along the first linear portion.

6. The medical implant apparatus according to claim 1, wherein the first linear portion is secured to the first rod member by only the positioning nut and the eye hook.

7. The medical implant apparatus according to claim 1, further comprising a securing nut coupled to the first linear portion such that the aperture of the eye hook is between the positioning nut and the securing nut.

8. A kit for total elbow arthroplasty, the kit comprising:
    the medical implant apparatus according to claim 1; and
    an antibiotic-loaded bone cement coated on the medical implant apparatus.

9. A method of treating a patient in need of total elbow arthroplasty, the method comprising:
    providing a medical implant apparatus comprising a first rod member that is substantially straight and a second rod member that is substantially straight;
    bending the second rod member to comprise a first linear portion, a second linear portion, and an arcuate portion;
    coupling an eye hook, which includes an aperture member, to the first rod member;
    inserting the first linear portion through the aperture member;
    coupling a positioning nut to the first linear portion;
    coating the first rod member and the second rod member with antibiotic-loaded bone cement; and
    implanting total elbow arthroplasty apparatus into the patient's elbow.

10. The method of treating a patient in need of total elbow arthroplasty according to claim 9, wherein the second linear portion of the second rod member is bent to correspond the alignment of the patient's proximal ulna and the proximal humerus.

11. The method of treating a patient in need of total elbow arthroplasty according to claim 9, wherein the arcuate portion is disposed between the first linear portion and the second linear portion.

12. The method of treating a patient in need of total elbow arthroplasty according to claim 9, wherein implantation of the total elbow arthroplasty apparatus includes implanting at least a portion of the first rod member into the patient's humerus and at least a portion of the second linear portion of the second rod into the patient's ulna.

13. The method of treating a patient in need of total elbow arthroplasty according to claim 9, further comprising removing an infected elbow prosthesis prior to implantation of the medical implant apparatus.

14. The method of treating a patient in need of total elbow arthroplasty according to claim 13, wherein after the medical implant apparatus is implanted for a predetermined period of time, further comprising removing the medical implant apparatus and implanting a permanent total elbow arthroplasty prosthesis.

15. The method of treating a patient in need of total elbow arthroplasty according to claim 9, wherein the first rod member is rotatably coupled to the second rod member.

16. The method of treating a patient in need of total elbow arthroplasty according to claim 9, wherein the medical implant apparatus provides the patient with an elbow range of motion of 0-145 degrees.

17. A medical implant apparatus for total elbow arthroplasty, the apparatus comprising:

a first rod member comprising a first nut, an eye hook, a first end, and a second end, wherein the first nut is disposed at the first end and the eye hook is disposed at the second end;

a second rod member rotatably coupled to the first rod member, the second rod member comprising a first linear portion, a second linear portion, and an arcuate portion disposed between the first linear portion and the second linear portion, the arcuate portion being configured to form a predetermined angle between the first rod member and the second rod member;

a positioning nut coupled to the first linear portion of the second rod member;

an aperture disposed in the eye hook; and a securing nut coupled to the first linear portion such that the aperture of the eye hook is between the positioning nut and the securing nut.

18. The medical implant apparatus according to claim 17, wherein the positioning nut is configured to adjust a position of the aperture of the eye hook along the first linear portion.

19. The medical implant apparatus according to claim 17, wherein the first linear portion is secured to the first rod member by the positioning nut and the eye hook.

20. A kit for total elbow arthroplasty, the kit comprising:
the medical implant apparatus according to claim 17; and
an antibiotic-loaded bone cement coated on the medical implant apparatus.

\* \* \* \* \*